(12) United States Patent
Naito et al.

(10) Patent No.: US 7,683,172 B2
(45) Date of Patent: Mar. 23, 2010

(54) UREA DERIVATIVE AND PROCESS FOR PREPARING THE SAME

(75) Inventors: Toshihiko Naito, Tsukuba (JP); Kazuhiro Yoshizawa, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 306 days.

(21) Appl. No.: 10/577,308

(22) PCT Filed: Nov. 8, 2004

(86) PCT No.: PCT/JP2004/016526

§ 371 (c)(1),
(2), (4) Date: Apr. 28, 2006

(87) PCT Pub. No.: WO2005/044788

PCT Pub. Date: May 19, 2005

(65) Prior Publication Data

US 2007/0037849 A1    Feb. 15, 2007

(30) Foreign Application Priority Data

Nov. 11, 2003  (JP)  ............... 2003-381249

(51) Int. Cl.
*C07D 215/20* (2006.01)
(52) U.S. Cl. .................................. 546/153
(58) Field of Classification Search .............. 546/153
See application file for complete search history.

(56) References Cited

U.S. PATENT DOCUMENTS

| | | | |
|---|---|---|---|
| 6,797,823 B1 | 9/2004 | Kubo et al. | |
| 7,169,789 B2 | 1/2007 | Kubo et al. | |
| 7,253,286 B2 * | 8/2007 | Funahashi et al. | 546/153 |
| 2004/0053908 A1 | 3/2004 | Funahashi | |
| 2004/0253205 A1 | 12/2004 | Yamamoto et al. | |
| 2007/0027318 A1 | 2/2007 | Kubo et al. | |

FOREIGN PATENT DOCUMENTS

| | | |
|---|---|---|
| EP | 1 698 623 A1 | 9/2006 |
| EP | 1 797 881 A1 | 6/2007 |
| JP | 8-48078 A | 2/1996 |
| JP | 11158149 A | 6/1999 |
| JP | 3712393 B2 | 11/2005 |
| JP | 2006-515884 A | 6/2006 |
| WO | WO-97/17329 | 5/1997 |
| WO | WO-98/00134 A1 | 1/1998 |
| WO | WO-99/32106 | 7/1999 |
| WO | WO-99/32436 | 7/1999 |
| WO | WO-00/42012 | 7/2000 |
| WO | WO-00/43366 A1 | 7/2000 |
| WO | WO-01/45689 A2 | 6/2001 |
| WO | WO-02/32872 A1 | 4/2002 |
| WO | WO-02/072578 A2 | 9/2002 |
| WO | WO-2004/064730 A2 | 8/2004 |
| WO | WO-2004/080462 A1 | 9/2004 |
| WO | WO-2004/080966 A1 | 9/2004 |
| WO | WO-2004/101526 A1 | 11/2004 |
| WO | WO-2005/063713 A1 | 7/2005 |
| WO | WO-2006/030826 A1 | 3/2006 |

OTHER PUBLICATIONS

Gardner, G. et al., Pesticide Biochemistry and Physiology, 1985, vol. 24, No. 3, pp. 285 to 297.
Nugiel, D.A., et al., Journal of Medicinal Chemistry, 2002, vol. 45, No. 24, pp. 5224 to 5232.

(Continued)

*Primary Examiner*—Peter G O'Sullivan
(74) *Attorney, Agent, or Firm*—Birch Stewart Kolasch & Birch LLP

(57) ABSTRACT

A process for preparing a compound (C) represented by the following formula:

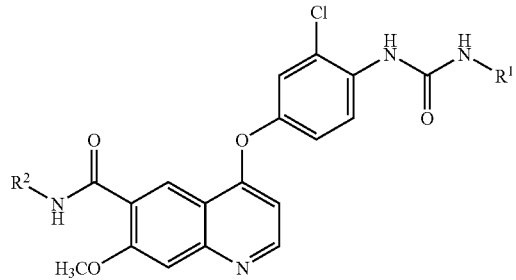

wherein $R^1$ represents hydrogen, $C_{1-6}$ alkyl or $C_{3-8}$ cycloalkyl, and $R^2$ represents hydrogen or methoxy, characterized by reacting a compound (A-1) represented by the following formula:

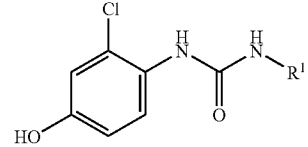

wherein $R^1$ has the same definition as above, with a compound (B) represented by the following formula:

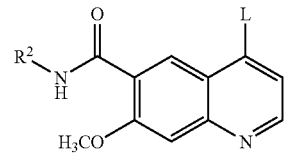

wherein $R^2$ has the same definition as above, and L represents a leaving group, is provided. Compound (C) is effective for prevention or treatment of various diseases associated with angiogenesis neoplasia.

9 Claims, No Drawings

OTHER PUBLICATIONS

Proceedings of the American Association for Cancer Research, vol. 45, Mar. 2004, pp. 1070-1071.

Gall-Istok et al., STN Accession No. 99:88018, Abstract of Acta Chimica Hungarica, 1983, vol. 122, No. 2, 241-247 (Abstract Only).

Cairns et al., "New antiallergic pyrano[3,2-g]quinoline-2,8-dicarboxylic acids with potential for the topical treatment of asthma", Journal of Medicinal Chemistry, 1985, vol. 28, pp. 1832-1842.

Abuzar et al., "Synthesis of some new 7-chloro-4-substituted quinolines as potential antiparasitic agents (1)", Eur. J. Med. Chem., vol. 21, No. 1, pp. 5-8 (1986).

Nocka et al., "Expression of c-kit gene products in known cellular targets of W mutations in normal and W mutant mice-evidence for an impaired c-kit kinase in mutant mice," Genes & Development, vol. 3, pp. 816-826 (1989).

Li et al., "Abrogation of c-kit/Steel factor-dependent Tumorigenesis by Kinase Defective Mutants of the c-kit Receptor: c-kit Kinase Defective Mutants as Candidate Tools for Cancer Gene Therapy," Cancer Research, vol. 56, pp. 4343-4346 (1996).

Office Action issued Aug. 20, 2009 in corresponding U.S. Appl. No. 10/797,903.

CancerCare, www.lungcancer/org/reading/types/php, 2009.

* cited by examiner

UREA DERIVATIVE AND PROCESS FOR PREPARING THE SAME

TECHNICAL FIELD

The present invention relates to urea derivatives which are effective for prevention or treatment of various diseases associated with abnormal angiogenesis, and to processes for preparing the same.

BACKGROUND ART

Urea derivatives represented by the general formula (C):
[Chemical Formula 1]

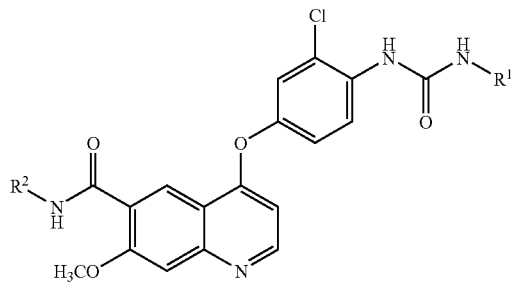

(C)

wherein $R^1$ represents hydrogen, $C_{1-6}$ alkyl or $C_{3-8}$ cycloalkyl, and $R^2$ represents hydrogen or methoxy, are known to exhibit excellent angiogenesis-inhibitory action (Patent document 1). Urea derivatives represented by general formula (C) also are known to exhibit powerful c-Kit kinase inhibitory action (Patent document 2, Non-patent document 1).

The preparing process described in Patent document 1 is useful as a process for preparing urea derivatives, but much room still remains for improvement in terms of total yield. It has therefore been desirable to develop an industrial process for preparing urea derivatives that gives a good total yield, as well as useful intermediates for such a preparing process.

Patent document 1 never discloses an efficient process for preparing urea compounds represented by the general formula (C), nor the useful intermediates represented by the general formulas (A-1) and (A-2), as according to the present invention.

Patent document 1: WO02/32872
Patent document 2: WO2004/080462
Non-patent document 1: 95th Annual Meeting Proceedings, AACR (American Association for Cancer Research), Volume 45, Page 1070-1071, 2004.

DISCLOSURE OF THE INVENTION

It is an object of the present invention to provide novel production intermediates of urea derivatives which are effective for prevention or treatment of various diseases associated with abnormal angiogenesis, as well as processes for their production.

As a result of much avid research in light of the circumstances described above, the present inventors discovered novel production intermediates of urea derivatives which are effective for prevention or treatment of various diseases associated with abnormal angiogenesis, as well as processes for their production, and have thereupon completed this invention. Specifically, the invention provides the following:

[1] A compound (A-1) or a salt thereof or a hydrate of the foregoing represented by the following formula:
[Chemical Formula 2]

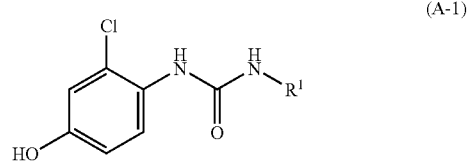

(A-1)

wherein $R^1$ represents hydrogen, $C_{1-6}$ alkyl or $C_{3-8}$ cycloalkyl.

[2] A compound or a salt thereof or a hydrate of the foregoing according to [1] wherein $R^1$ is hydrogen, methyl, ethyl, n-propyl or cyclopropyl;

[3] A compound or a salt thereof or a hydrate of the foregoing according to [1] wherein $R^1$ is cyclopropyl;

[4] A process for preparing a compound (A-1) represented by the following formula:
[Chemical Formula 6]

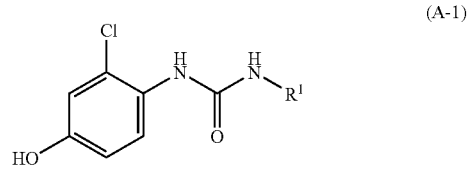

(A-1)

wherein $R^1$ has the same definition as above, characterized by reacting a compound (A-3) represented by the following formula:
[Chemical Formula 3]

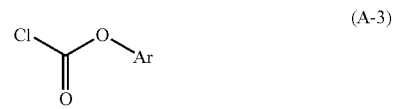

(A-3)

wherein Ar represents $C_{6-10}$ aryl optionally having 1 or 2 substituents selected from the group consisting of halogen, methyl, methoxy and nitro, with a compound (A-4) represented by the following formula:
[Chemical Formula 4]

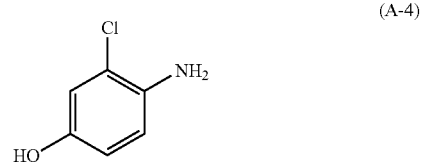

(A-4)

to afford a compound (A-2) represented by the following formula:

[Chemical Formula 5]

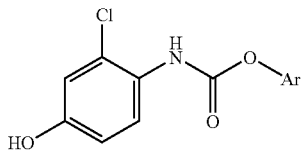

(A-2)

wherein Ar has the same definition as above, and then reacting the compound (A-2) with a compound represented by the formula $R^1$—$NH_2$, wherein $R^1$ has the same definition as above;

[5] A process according to [4], wherein $R^1$ is hydrogen, methyl, ethyl, n-propyl or cyclopropyl;

[6] A process according to [4], wherein $R^1$ is cyclopropyl;

[7] A process according to any one of [4] to [6], wherein Ar is phenyl;

[8] A compound (A-2) or a salt thereof or a hydrate of the foregoing represented by the following formula:

[Chemical Formula 7]

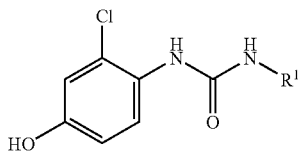

(A-1)

wherein Ar has the same definition as above;

[9] A compound or a salt thereof or a hydrate of the foregoing according to [8], wherein Ar is phenyl;

[10] A process for preparing compound (C) or a salt thereof represented by the following formula:

[Chemical Formula 10]

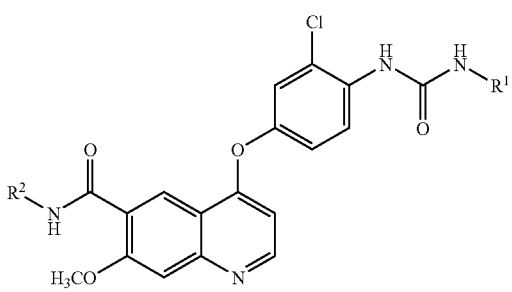

(C)

wherein $R^1$ and $R^2$ have the same definitions as above, characterized by reacting a compound (A-1) represented by the following formula:

[Chemical Formula 8]

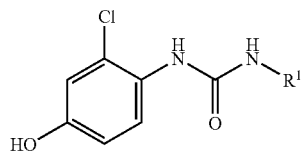

(A-1)

wherein $R^1$ has the same definition as above, with a compound (B) represented by the following formula:

[Chemical Formula 9]

(B)

wherein $R^2$ represents hydrogen or methoxy, and L represents a leaving group;

[11] A process according to [10], characterized by using a base;

[12] A process according to [11], wherein the base is an alkali metal carbonate or an alkali metal alkoxide;

[13] A process according to [11], wherein the base is cesium carbonate, potassium carbonate or potassium t-butoxide;

[14] A process according to any one of [10] to [13], wherein $R^1$ is hydrogen, methyl, ethyl, n-propyl or cyclopropyl;

[15] A process according to any one of [10] to [13], wherein $R^1$ is cyclopropyl;

[16] A process according to any one of [10] to [15], wherein $R^2$ is hydrogen;

[17] A process according to any one of [10] to [16], wherein L is chlorine.

BEST MODE FOR CARRYING OUT THE INVENTION

The present invention will now be explained in detail, including explanations of the meanings of the terms and symbols used throughout the present specification.

The compounds or salts of the invention may be anhydrates, hydrates or solvates.

The term "$C_{1-6}$ alkyl" as used throughout the present specification refers to a monovalent group derived by removing any hydrogen atom from a C1-6 aliphatic hydrocarbon. It is a C1-6 straight- or branched-chain alkyl group, and as specific examples there may be mentioned methyl, ethyl, n-propyl, isopropyl, n-butyl, isobutyl, sec-butyl, tert-butyl, n-pentyl, isopentyl, sec-pentyl, neopentyl, 1-methylbutyl, 2-methylbutyl, 1,1-dimethylpropyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, among which methyl, ethyl and n-propyl are preferred.

The term "$C_{3-8}$ cycloalkyl" as used throughout the present specification refers to a C3-8 cyclic aliphatic hydrocarbon group, and as specific examples there may be mentioned cyclopropyl, cyclobutyl, cyclopentyl, cyclohexyl, cycloheptyl and cyclooctyl, among which cyclopropyl is preferred.

The term "$C_{6-10}$ aryl" as used throughout the present specification refers to a C6-10 aromatic hydrocarbon ring group, and as specific examples there may be mentioned phenyl, 1-naphthyl and 2-naphthyl, among which phenyl is preferred.

The term "halogen" as used throughout the present specification refers to fluorine, chlorine, bromine or iodine, among which chlorine is preferred.

The term "base" as used throughout the present specification refers to an organic base (for example, pyridine, 2,6-lutidine, collidine, triethylamine, diisopropylethylamine, diazabicyclo[5.4.0]undec-7-ene, etc.) or an inorganic base (an alkali metal carbonate (for example, cesium carbonate, potassium carbonate, sodium carbonate, etc.), an alkali metal alkoxide (for example, potassium t-butoxide, sodium ethoxide, etc.), an alkali metal hydride (for example, potassium hydride, sodium hydride, etc.), or an alkali metal hydroxide (for example, potassium hydroxide, sodium hydroxide, etc.). The base used in the step of reacting a compound (A-1) with a compound (B) to afford compound (C) is preferably an alkali metal carbonate or an alkali metal alkoxide, and more preferably cesium carbonate, potassium carbonate or potassium t-butoxide.

As examples of "salts" referred to throughout the present specification there may be mentioned inorganic acid salts, organic acid salts, inorganic base salts, organic base salts, and acidic or basic amino acid salts.

As preferred examples of inorganic acid salts there may be mentioned salts with hydrochloric acid, hydrobromic acid, sulfuric acid, nitric acid and phosphoric acid, and as preferred examples of organic acid salts there may be mentioned salts with acetic acid, succinic acid, fumaric acid, maleic acid, tartaric acid, citric acid, lactic acid, stearic acid, benzoic acid, methanesulfonic acid, ethanesulfonic acid and p-toluenesulfonic acid.

As preferred examples of inorganic base salts there may be mentioned alkali metal salts such as sodium salts and potassium salts, alkaline earth metal salts such as calcium salts and magnesium salts, and aluminum salts or ammonium salts. As preferred examples of organic base salts there may be mentioned salts with diethylamine, diethanolamine, meglumine and N,N-dibenzylethylenediamine.

As preferred examples of acidic amino acid salts there may be mentioned salts with aspartic acid and glutamic acid, and as preferred examples of basic amino acid salts there may be mentioned salts with arginine, lysine and ornithine.

The term "leaving group" as used throughout the present specification may be any group which is usually known as a leaving group in organic synthesis, without any particular restrictions, and as specific examples there may be mentioned halogens such as chlorine, bromine and iodine, alkylsulfonyloxy groups such as methanesulfonyloxy, trifluoromethanesulfonyloxy and ethanesulfonyloxy, arylsulfonyloxy groups such as benzenesulfonyloxy and p-toluenesulfonyloxy, alkoxy groups such as methoxy and ethoxy, and alkylthio groups such as methylthio and ethylthio. Preferred "leaving groups" are halogens such as chlorine, bromine and iodine, with chlorine being especially preferred.

Preparing processes according to the invention will now be explained in detail.

Preparing Process 1, Process for Preparing Urea (A-1)

[Chemical Formula 11]

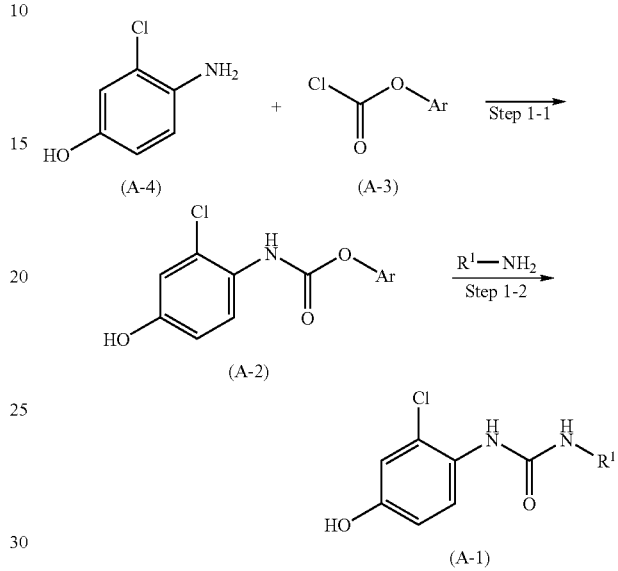

wherein the symbols have the same definitions as above.

[Step 1-1]

This is a step of reacting a carbamating reagent (A-3) such as phenyl chloroformate with a compound (A-4) to afford a compound (A-2). The reaction solvent used may be dimethylsulfoxide, N,N-dimethylformamide, N,N-dimethylacetamide, tetrahydrofuran, ethyl acetate or the like. The reaction may also utilize a base such as pyridine. The carbamating reagent (A-3) is used at 1-2 equivalents with respect to the compound (A-4). The base is used at 1-4 equivalents with respect to the compound (A-4). The reaction time is from 10 minutes to 30 hours. The reaction temperature is from 0° C. to heated reflux temperature, and is preferably between 0° C. and room temperature.

[Step 1-2]

This is a step of reacting an amine derivative $R^1$—$NH_2$ with the compound (A-2) to afford a compound (A-1). The reaction solvent used may be dimethylsulfoxide, N,N-dimethylformamide, N,N-dimethylacetamide, tetrahydrofuran, ethyl acetate, acetonitrile, toluene, chloroform or the like. The reaction may also utilize an organic base (for example, pyridine, triethylamine, diisopropylethylamine, etc.) or inorganic base (an alkali metal carbonate (for example, cesium carbonate, potassium carbonate, sodium carbonate, etc.) or an alkali metal hydride (for example, potassium hydride, sodium hydride, etc.)). The amine derivative is used at 1-3 equivalents with respect to the compound (A-2). The base is used at 1-3 equivalents with respect to the compound (A-2). The reaction time is from 10 minutes to 30 hours. The reaction temperature is from 0° C. to heated reflux temperature, and is preferably between 0° C. and room temperature.

Preparing Process 2, Process for Preparing Compound (C)

[Chemical Formula 12]

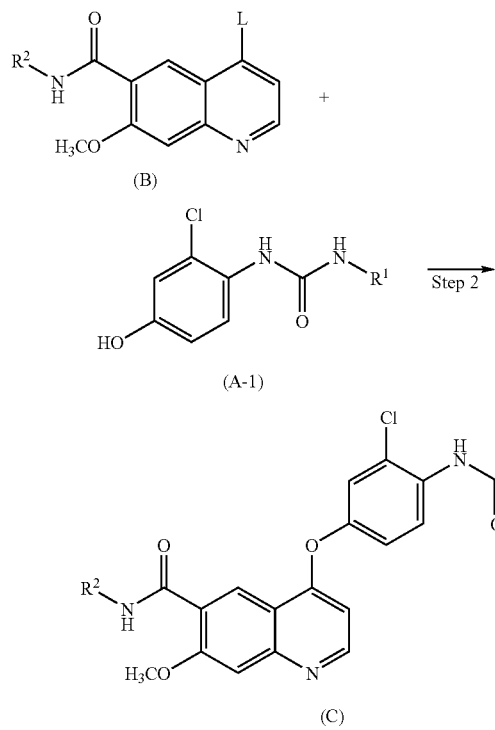

wherein the symbols have the same definitions as above.

[Step 2]

This is a step of reacting a compound (A-1) with a compound (B) to afford a compound (C). The reaction solvent used may be 1-methylpyrrolidone, dimethylsulfoxide, N,N-dimethylformamide, N,N-dimethylacetamide, 1,3-dimethyl-2-imidazolidinone, toluene, chlorobenzene or the like. As appropriate bases there may be added an organic base (for example, pyridine, 2,6-lutidine, collidine, triethylamine, diisopropylethylamine, diazabicyclo[5.4.0]undec-7-ene, etc.) or an inorganic base (an alkali metal carbonate (for example, cesium carbonate, potassium carbonate, sodium carbonate, etc.), an alkali metal alkoxide (for example, potassium t-butoxide, sodium ethoxide, etc.), an alkali metal hydride (for example, potassium hydride, sodium hydride, etc.), or an alkali metal hydroxide (for example, potassium hydroxide, sodium hydroxide, etc)). As such bases there are preferred alkali metal carbonates and alkali metal alkoxides, among which cesium carbonate, potassium carbonate and potassium t-butoxide are especially preferred. The compound (A-1) is used at 1-2 equivalents with respect to the compound (B). The base is used at 1-2 equivalents with respect to the compound (B). The reaction time is from 10 minutes to 48 hours. The reaction temperature is from room temperature to heated reflux temperature, and is preferably between 40° C. and 80° C.

Upon completion of the reaction, purification may be performed if necessary by an ordinary treatment method, for example, column chromatography using silica gel or an adsorption resin, or by recrystallization from an appropriate solvent.

EXAMPLES

Examples will now be described to facilitate understanding of the invention, but the invention is not limited to these examples.

Example 1

Phenyl N-(2-chloro-4-hydroxyphenyl)carbamate

[Chemical Formula 13]

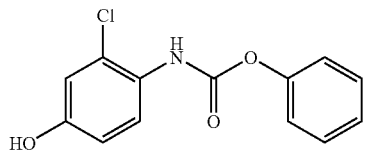

After suspending 4-amino-3-chlorophenol (23.7 g) in N,N-dimethylformamide (100 mL) and adding pyridine (23.4 mL) while cooling on ice, phenyl chloroformate (23.2 ml) was added dropwise below 20° C. Stirring was performed at room temperature for 30 minutes, and then water (400 mL), ethyl acetate (300 mL) and 6N HCl (48 mL) were added, the mixture was stirred and the organic layer was separated. The organic layer was washed twice with 10% brine (200 mL), and dried over magnesium sulfate. The solvent was removed to give 46 g of the title compound as a solid.

$^1$H-NMR(CDCl$_3$): 5.12(1 h, br s), 6.75(1H, dd, J=9.2, 2.8 Hz), 6.92(1H, d, J=2.8 Hz), 7.18-7.28(4H, m), 7.37-7.43(2H, m), 7.94(1H, br s)

Example 2

1-(2-chloro-4-hydroxyphenyl)-3-cyclopropylurea

[Chemical Formula 14]

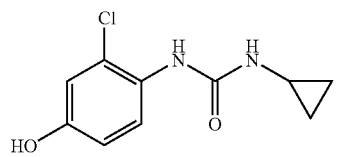

After dissolving phenyl N-(2-chloro-4-hydroxyphenyl)carbamate in N,N-dimethylformamide (100 mL), cyclopropylamine (22.7 mL) was added while cooling on ice and the mixture was stirred overnight at room temperature. Water (400 mL), ethyl acetate (300 mL) and 6N HCl (55 mL) were then added, the mixture was stirred and the organic layer was separated. The organic layer was washed twice with 10% brine (200 mL), and dried over magnesium sulfate. Prism crystals obtained by concentrating the solvent were filtered and washed with heptane to give 22.8 g of the title compound (77% yield from 4-amino-3-chlorophenol).

$^1$H-NMR(CDCl$_3$): 0.72-0.77(2H, m), 0.87-0.95(2H, m), 2.60-2.65(1H, m), 4.89(1H, br s), 5.60(1H, br s), 6.71(1H, dd, J=8.8, 2.8 Hz), 6.88(1H, d, J=2.8 Hz), 7.24-7.30(1H, br s), 7.90(1H, d, J=8.8H)

Example 3

4-(3-chloro-4-(cyclopropylaminocarbonyl)aminophenoxy)-7-methoxy-6-quinolinecarboxamide

[Chemical Formula 15]

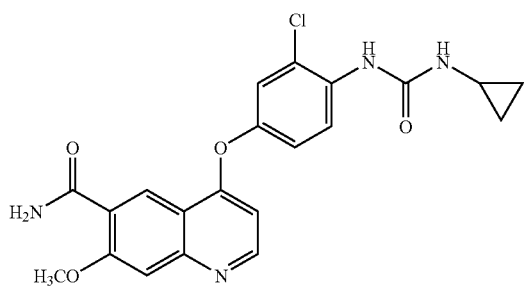

To dimethylsulfoxide (20 mL) were added 7-methoxy-4-chloro-quinoline-6-carboxamide (0.983 g), 1-(2-chloro-4-hydroxyphenyl)-3-cyclopropylurea (1.13 g) and cesium carbonate (2.71 g), followed by heating and stirring at 70° C. for 23 hours. After the reaction mixture was allowed to cool down to room temperature, water (50 mL) was added, and the produced crystals were collected by filtration to give 1.56 g of the title compound (88% yield).

$^1$H-NMR($d_6$-DMSO): 0.41(2H, m), 0.66(2H, m), 2.56(1H, m), 4.01(3H, s), 6.51(1H, d, J=5.6 Hz), 7.18(1H, d, J=2.8 Hz), 7.23(1H, dd, J=2.8, 8.8 Hz), 7.48(1H, d, J=2.8 Hz), 7.50(1H, s), 7.72(1H, s), 7.84(1H, s), 7.97(1H, s), 8.25(1H, d, J=8.8 Hz), 8.64(1H, s), 8.65(1H, d, J=5.6 Hz)

Example 4

4-(3-chloro-4-(cyclopropylaminocarbonyl)aminophenoxy)-7-methoxy-6-quinolinecarboxamide In a reaction vessel were placed 7-methoxy-4-chloro-quinoline-6-carboxamide (5.00 kg, 21.13 mol), dimethylsulfoxide (55.05 kg), 1-(2-chloro-4-hydroxyphenyl)-3-cyclopropylurea (5.75 kg, 25.35 mol) and potassium t-butoxide (2.85 kg, 25.35 mol) in that order, under a nitrogen atmosphere. After stirring at 20° C. for 30 minutes, the temperature was raised to 65° C. over a period of 2.5 hours. After stirring at the same temperature for 19 hours, 33% (v/v) acetone water (5.0 L) and water (10.0 L) were added dropwise over a period of 3.5 hours. Upon completion of the dropwise addition, the mixture was stirred at 60° C. for 2 hours, and 33% (v/v) acetone water (20.0 L) and water (40.0 L) were added dropwise at 55° C. or higher over a period of 1 hour. After then stirring at 40° C. for 16 hours, the precipitated crystals were collected by filtration using a nitrogen pressure filter, and the crystals were washed with 33% (v/v) acetone water (33.3 L), water (66.7 L) and acetone (50.0 L) in that order. The obtained crystals were dried at 60° C. for 22 hours using a conical vacuum drier to give 7.78 kg of the title compound (96.3% yield).

The processes for preparing urea derivatives according to the invention allow efficient production of urea derivatives, which are effective for prevention or treatment of various diseases associated with abnormal angiogenesis, by industrial preparing processes. The urea derivative intermediates according to the invention are useful as intermediates for efficient production of the aforementioned urea derivatives.

INDUSTRIAL APPLICABILITY

The processes for preparing urea derivatives according to the invention allow efficient production of urea derivatives, which are effective for prevention or treatment of various diseases associated with abnormal angiogenesis, by industrial preparing processes. The urea derivative intermediates according to the invention are useful as intermediates for efficient production of the aforementioned urea derivatives.

The invention claimed is:

1. A process for preparing a compound (C) or a salt thereof represented by the following formula:

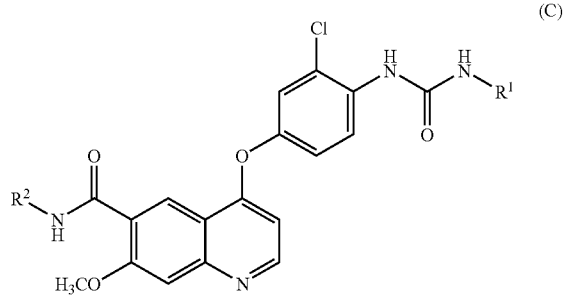

(C)

wherein $R^1$ represents hydrogen, $C_{1-6}$ alkyl or $C_{3-8}$ cycloalkyl, and wherein $R^2$ represents hydrogen or methoxy, said method comprising reacting a compound (A-1) represented by the following formula:

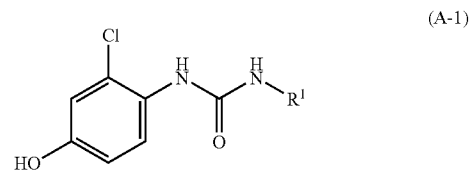

(A-1)

wherein $R^1$ has the same definition as above, with a compound (B) represented by the following formula:

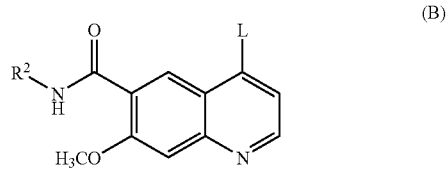

(B)

wherein $R^2$ is defined as above, and L represents a leaving group.

2. A process according to claim 1, wherein the reaction is performed in the presence of a base.

3. A process according to claim 2, wherein the base is an alkali metal carbonate or an alkali metal alkoxide.

4. A process according to claim 2, wherein the base is cesium carbonate, potassium carbonate or potassium t-butoxide.

5. A process according to claim 1, wherein $R^1$ is hydrogen, methyl, ethyl, n-propyl or cyclopropyl.

6. A process according to claim 1, wherein $R^1$ is cyclopropyl.

7. A process according to claim 1, wherein $R^2$ is hydrogen.

8. A process according to claim 1, wherein L is chlorine.

9. A process according to claim 1, wherein the reaction is performed in dimethylsulfoxide in the presence of cesium carbonate or potassium t-butoxide.

* * * * *